March 27, 1962 Q. MANSUINO Plant Pat. 2,134
ROSE PLANT
Filed Feb. 8, 1961
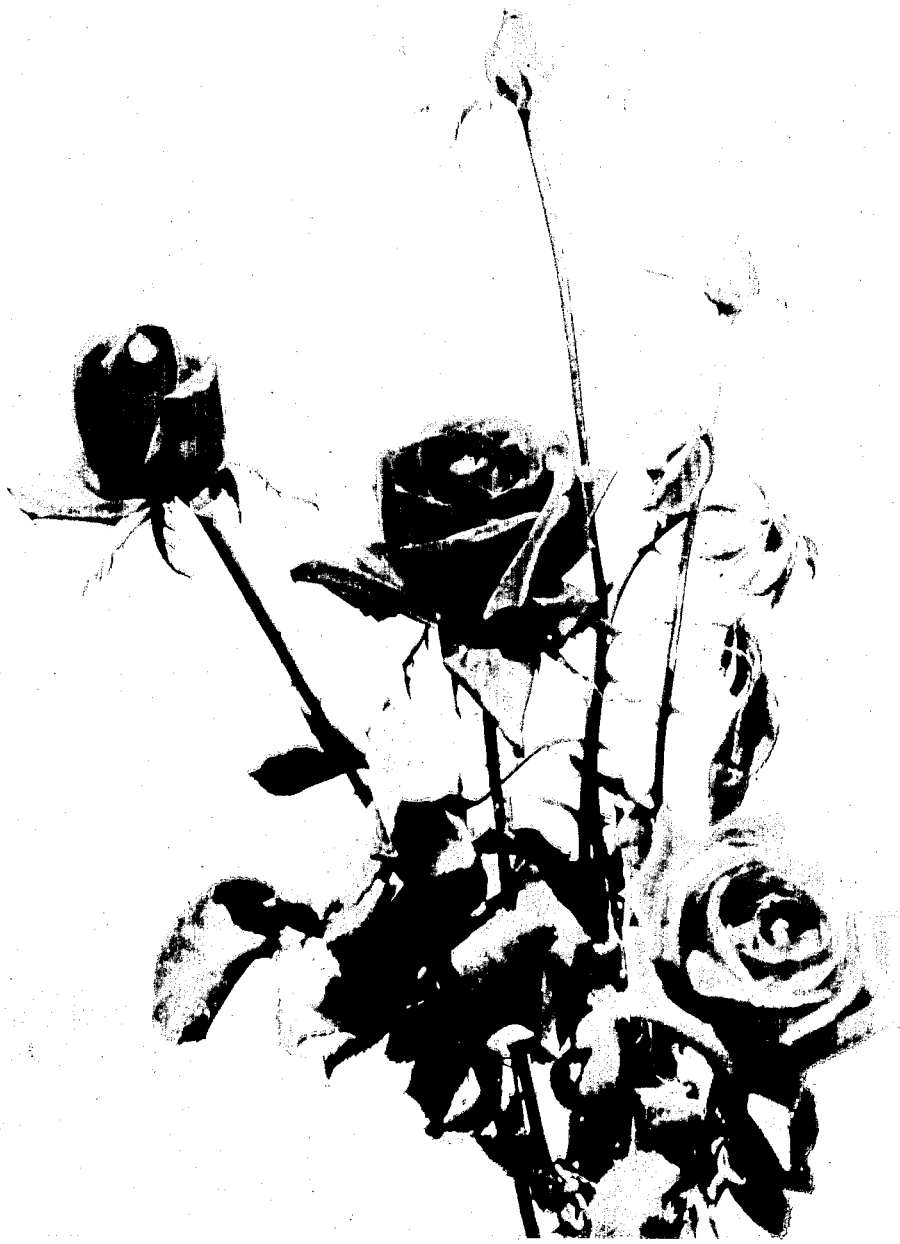
INVENTOR
Quinto Mansuino
BY Robb & Robb
ATTORNEYS United States Patent Office Plant Pat. 2,134
Patented Mar. 27, 1962

2,134
ROSE PLANT

Quinto Mansuino, Via Duca d'Aosta 15, Sanremo, Italy

Filed Feb. 8, 1961, Ser. No. 87,982
Claims priority, application Italy Feb. 29, 1960
1 Claim. (Cl. 47—61)

The present invention relates to a new and distinct variety of rose plant of the hybrid tea class, which was originated by me by crossing an unnamed and unpatented seedling derived from a cross of the variety named "Vierlanden" (unpatented)×the variety named "Gloria di Roma" (U.S. Plant Patent No. 304) with the variety named "Baccara" (U.S. Plant Patent No. 1367).

The primary objectives of this breeding were to produce a new rose variety having the following general characteristics: A thick, dense, rapid growing habit; abundant and attractive disease resistant foliage; a very free blooming habit; good productiveness suitable for commercial cultures; long and strong, moderately thorny, erect, straight and slender stems; a large flower size; an attractive and decorative flower form; velvety flower petals; and a distinctive and attractive flower color in the red color range, said red color being free from any tendancy to turn blue as occurs with many other red rose varieties.

As the result of the breeding of my new rose variety referred to above, most of the aforementioned objectives were achieved, along with other improvements, as evidenced by the following characteristics which are outstanding in the new variety:

(1) A vigorous, erect, bushy and rapid growing habit;
(2) Abundant and attractive glossy foliage;
(3) An extremely free and abundant blooming habit throughout the year, which makes the variety especially suitable for the production of cut ffowers and also for decorative garden plants all year around;
(4) A habit of bearing the flowers singly on long, erect, stiff and stout stems of only moderate thorniness, thus making the new variety especially suitable for cut flowers;
(5) An attractive and decorative flower form;
(6) A large flower size;
(7) Flower petals of velvety texture;
(8) A distinctive and attractive flower color corresponding to Cardinal Red in general color tonality, overlaid and blended with Currant Red color; and
(9) Freedom of bluish flower tones.

The foregoing characteristics definitely distinguish my new variety from its parents, as well as from all other varieties of which I am aware, and asexual reproduction thereof by budding, as performed by me at Sanremo, Italy, shows that these characteristics and distinctions come true to form and are established and transmitted through succeeding propagations.

The accompanying drawing shows typical specimens of the vegetative growth and flowers of my new variety in different stages of development and as depicted in color.

The following is a detailed description of my new variety, with color terminology in accordance with Robert F. Wilson's Horticultural Colour Chart, except where general color terms of ordinary dictionary significance are obvious:

Parentage: Seedling.
*Seed parent.*—An unnamed seedling derived from a salmon colored rose named "Vierlanden"×the red flowered rose variety named "Gloria di Roma" ("Rome Glory" in the United States).
*Pollen parent.*—"Baccara."

Classification:
*Botanic.*—Hybrid tea.
*Commercial.*—Hybrid tea.

*Plant*

(Observations made from specimens grown outdoors at Sanremo, Italy.)

Growing habit: Bushy; erect; dense; compact; well-clothed by large, glossy foliage, with a free and abundant blooming habit.
*Height.*—From 5 to 6 feet tall after one year growth on *Rosa indica* major understock.
*Roots.*—Variable; generally strong; much-branched; from about 1¾ to 2 feet long and from about ¼ to ½ inch in diameter.
*Stalk.*—Strong; erect; cylindrical; variable in size, but generally short; from about ½ to ¾ inch in diameter at the grafting point.
*Branches.*—From moderately numerous to numerous; generally from 3 to 8, starting from the grafting point; arranged at very short intervals; variously branches according to the cutting system employed; branched moderately divergent and almost horizontal at their base, but quickly becoming oblique or vertical. Size—variable according to cutting system; average length from 1 to 2 feet; average diameter at base from ¼ to ½ inch.
*Thorns.*—Numerous; scattered; thick; single but sometimes coupled. Shape—triangular; long; generally straight, but sometimes slightly hooked downwards; with moderately acute point; with oval base. Size—variable; usually from about ⅜ to ⅝ of an inch long and from about ¼ to ½ inch broad. Texture—woody. Color—dark hazelnut, sometimes shaded with reddish brown.

Floral stems: Numerous; average from 6 to 10 in fully grown plants; erect, but moderately divergent; moderately thin and slender.
*Shape.*—Nearly cylindrical; usually straight, but sometimes slightly sinuous; articulated in numerous long and slender internodes, with each intermode being from 2½ to 4 inches long.
*Size.*—Average length from about 2 to 3 feet; average diameter at base from about ¼ to ⅜ inch.
*Bark.*—Smooth; glabrous; satiny or slightly pruinous.
*Color.*—Between Spinach Green, Plates 60/1 and 60/2, page 187, strongly covered and shaded with between Maroon, Plates 30/1 and 30/2, page 185, and Pansy Purple, Plates 28/2 and 28/3, page 177; more intensive and spread on the new shoots and floral peduncles.
*Thorns.*—From moderately numerous to numerous; more numerous on the lower part of the stems. Shape—from medium length to long; medium narrow; with acute point; usually nearly horizontal but sometimes slightly hooked downwards; triangular, with the under side more hooked than the upper side; asymmetrical. Texture—moderately tender; slightly transparent; easily detachable from the bark. Size—variable, according to the position on the stem; average length from about ⅜ to ½ inch; average breadth from about ¼ to ⅜ inch; average thickness from about ⅛ to ¼ inch. Color—nearly transparent Maroon, ranging from Plates 30, through 30/3, page 185, sometimes slightly softened with yellowish green on the points.
*Knots.*—Little variation; each bearing a leaf and an axillary bud.

Leaves: Abundant; large; stout; cover plant and floral stems in a very full and attractive manner; scattered on the stem and on the branches; moderately divergent from the stem to nearly horizontal.
*Shape.*—Compound of 1—3—5—7 leaflets, but usually 5; borne on strong rachis at slightly irregular intervals; arranged opposite, with a single terminal leaflet.

*Size.*—Large; generally from 4 to 6 inches long from the base to the end of the terminal leaflet; from 4 to 5 inches broad between the extreme points of the opposite lateral leaflets.

*Leaflets.*—Large; slightly undulated; rounded oval shape; slightly lanceolate; with slightly variable point; edges characteristically undulated like a holly leaf; finely dentate; with thin, acute teeth towards the point of the leaflet; central longitudinal rib, with thin pennated lateral veins slightly recessed in the upper face of the leaflet and slightly protruding on the under face. Size—increasing from the first pair of leaflets near the base of the rachis toward the terminal leaflet as follows: first pair—length from about ¾ to 1¼ inches; breadth from about ¾ to 1 inch; second pair—length from about 1¼ to 1½ inches; breadth from about 1¼ to 1½ inches; third pair—length from about 2 to 2½ inches; breadth from about 1¼ to 1¾ inches; terminal leaflet—length from 2½ to 3¼ inches.

*Color.*—Upper surface: old leaves—between Parsley Green, Plates 62 to 62/3, page 193, and Ivy Green, Plate 60/3, pate 200; new leaves—near Fern Green, Plates 62/1 to 62/3, page 186, with veins and shades of color ranging between Pansy Purple, Plate 28/3, page 177, and Garnet Lake, Plate 28/3, page 172. Under surface: old leaves—between Willow Green, Plates 62/1 and 62/2, page 199, and Sage Green, Plates 61/1 to 61/3, page 198, often shaded with between Pansy Purple, Plate 28/3, page 177, and light Garnet Lake, Plate 28/3, page 172; new leaves—Fern Green, Plate 68/1, page 186, strongly shaded with Garnet Lake, Plate 28/3, page 172.

*Texture.*—Young leaves—from thin to medium thin; leathery. Old leaves—medium thick; leathery.

*Rachis.*—From thin to stout; sinuous or slightly angular; nearly half cylindrical; with a small, deep longitudinal recess having protruding edges; bears short and thin hairs; slightly swollen at the intersection point of the leaflet peduncle. Color—Parsley Green, Plates 62 and 62/1, page 193, often strongly overlaid with Maroon, Plates 30/1 and 30/2, page 185, on the upper surface, and near Willow Green, Plates 60/2 and 60/3, page 199, strongly shaded with Pansy Purple, Plates 28/2 and 28/3, page 177, on the lower face.

*Peduncles of leaflets.*—Very short; from ⅛ to ¼ inch long.

*Stipules.*—From few to medium; adnascent, with the rachis over about ½ the interval between the attachment and the insertion of the first pair of leaflets; narrow; thin; foliaceous; with medium points averaging from ⅛ to 3/16 inch long; moderately turning out from the rachis; with slightly hairy edges.

*Flower*

Flowers borne: Singly; erect; on slightly variable, rigid and somewhat slightly sinuous peduncle averaging from 3 to 4 inches long; with numerous short, tender, acutely pointed prickles; the leaves of the last knot under the floral peduncle are often rudimentary and the terminal flower is often accompanied by from 2 to 4 small floral buds that are smaller and shorter than the primary flower.

Bud:

*Shape.*—Ovoid; elongated; with medium variability of receptacle; acutely pointed; bearing foliaceous appendages behind the point of the bud; with many, short, thin and slightly lanceolate lateral appendages on the edges of the sepals turning out from the bud.

*Size (when sepals break).*—Length—from 1½ to 1¾ inches. Diameter—from ⅝ to ¾ inch.

*Color.*—Near Willow Green, Plates 62/1 and 62/2, page 199, more or less shaded with Pansy Purple, Plates 28/2 and 28/3, page 177, and with Garnet Lake, Plate 28/3, page 172, especially on the new buds.

*Receptacle (when bloom is open).*—Medium developed; open-cupped; slightly variable; about ¼ to ⅜ inch long and about ½ to ⅝ inch in diameter. Color—strongly colored with near Garnet Lake, Plate 28/3, page 172.

*Sepals.*—5 in number; medium size; more or less falling on the receptacle when the bloom opens. Shape—triangular; elongated; slightly lanceolate; lateral margins smooth and slightly tomentous, and sometimes bearing thin foliaceous appendages about ¼ to ⅜ inch long and about 1/32 inch broad and turning out from the sepal edges; other appendages on the point of the sepals. Size—medium length (from about 1¼ to 1¾ inches); medium width (from about ⅜ to ½ inch at base). Color—upper surface near Fern Green, Plates 62 and 62/1, page 186, shaded and spotted at the base of each sepal with short whitish tomentum.

Bud (as first petal opens):

*Shape.*—Irregularly urn-shaped, with the upper edge of the petals slightly curled outwards.

*Size.*—Average length from 2 to 2½ inches; average diameter from 1⅛ to 2 inches.

*Color.*—Outer petals—near Purple Madder, Plate 28, page 181. Inner petals—near Chrysanthemum Purple, Plates 24 and 24/1, page 169, with tones of Oxblood Red, Plate 23, page 191.

Bloom:

*Shape.*—Cup-shaped and high-centered at first, but becoming more concave when the flowers open; outer petals disposed horizontally or slightly inclined downwardly on the receptacle and slightly or medium curled outwards; intermediate and central petals are slightly curved outwards when the bloom opens, becoming medium curled on lateral edges forming medium protruding points when the curling of the petals meet each other.

*Size.*—Average diameter from 5½ to 6½ inches when fully opened.

*General color tonality.*—Cardinal Red, Plates 22 and 22/1, page 168, with velvety overlay of Currant Red, Plates 21/1 and 21/3, page 167, which later becomes spread entirely over the bloom when it matures.

Petals: Medium number (average from about 20 to 30).

*Shape.*—Outer petals—large; concave in the center; rounded oval; slightly triangular near the attachment; with lateral margins slightly reflexed and making medium points that give to the petal a square shape; with medium thick, short and stout attachment; size—large; medium length (from about 2½ to 3¾ inches); medium width (from about 2½ to 3¾ inches). Intermediate and inner petals—large; irregular; often with a central longitudinal vein; margins often reflexed toward the center of the bloom; outer margins irregular and some having a few deep notches; with small, stout, slightly variable attachment; size (inner petals)—medium length (from about 1½ to 2½ inches); medium width (from about 1¼ to 1½ inches). Color: upper surface—between Currant Red, Plates 21/1 to 21/3, page 167, and Cardinal Red, Plates 22/1 to 22/3, page 168, overcast with Rose Red, Plates 24/1 to 24/3, page 158, near attachment, and shading to Chrysanthemum Crimson, Plates 24/2 and 24/3, page 169, near the edges; under surface—between Chrysanthemum Crimson, Plates 24/1 to 24/3, page 169, and Cardinal Red, Plates 22/2 and 22/3, page 168. Attachment—near Empire Yellow, Plates 3/1 to 3/3, page 66. Surface: upper face—velvety with change in color; with thin veins; fan-shaped; slightly hollowed; under face—smooth; satiny; with well defined fan-spread veins which protrude slightly; texture—thick; fleshy; stiff.

Fragrance: From slight to medium. Nature—sweet; tea.

Disease resistance: Very good resistance to blackspot and mildew, as determined by comparison with other varieties grown under comparable conditions at Sanremo, Italy.

Handling and shipping qualities: Very good.

Flower longevity: Remarkably long.

Quantity of bloom: Very abundant; continuous.

*Reproductive Organs*

Stamens: Numerous (averaging from 120 to 150); arranged on the edge of the receptacle and around the styles.

Filaments: Robust; erect; from ½ to ¾ inch long; a few curved toward the center of the flower. Color—near Delft Rose, Plates 20/1 and 20/2, page 108.

Anthers: From medium size to large; oval; elongated biloculate. Color—near Chrome Yellow, Plate 5/1, page 144.

Ovaries: Almost entirely enclosed in the receptacle; with thick hairs on the base of styles.

Styles: Numerous (average from 100 to 120); narrowed at base; medium free at apex. Color—greenish, shaded with purple.

Stigmas: Conical in shape. Color—near Chrome Yellow, Plate 5/1, page 144.

I claim:

A new and distinct variety of rose plant of the hybrid tea class, substantially as herein shown and described, characterized particularly as to novelty by the unique combination of a vigorous, bushy, erect and rapid habit of growth, abundant and attractive, large, glossy foliage which clothes the plant well, an extremely free and abundant blooming habit throughout the year, with consequent suitability for use for commercial cut flower production, as well as for decorative garden plants, a habit of bearing the flowers singly on long, erect, rigid and stout stems, an attractive and decorative flower shape, large flower size, velvety flower petals, a distinctive and attractive general color tonality of the flowers corresponding to Cardinal Red overlaid with Currant Red, and relatively complete freedom of bluing tendency of the flower colors.

No references cited.